United States Patent [19]

Swaniger

[11] Patent Number: 4,769,011
[45] Date of Patent: Sep. 6, 1988

[54] SYRINGE APPARATUS AND METHOD FOR THE SURGICAL IMPLANTATION OF GRANULAR SUBSTANCES

[75] Inventor: James R. Swaniger, Irvine, Calif.

[73] Assignee: Interpore International, Inc., Irvine, Calif.

[21] Appl. No.: 717,892

[22] Filed: Mar. 28, 1985

[51] Int. Cl.$^4$ ............................................. A61M 25/00
[52] U.S. Cl. ...................................... 604/218; 604/60
[58] Field of Search .................... 604/218, 15, 18, 55, 604/59, 60, 264, 271, 280, 228

[56] References Cited

U.S. PATENT DOCUMENTS

| | | | |
|---|---|---|---|
| 1,608,275 | 11/1926 | Grier et al. | 604/218 |
| 2,007,626 | 7/1935 | Waring | 604/218 |
| 2,009,393 | 7/1935 | Failla | 604/60 |
| 2,170,599 | 8/1939 | Stricklen | 604/218 |
| 2,630,804 | 3/1953 | Mende | 604/59 |
| 3,297,031 | 1/1967 | Bray | 604/218 |
| 3,401,689 | 9/1968 | Greenwood | 604/55 |
| 3,642,000 | 2/1972 | Baker | 604/218 |
| 4,068,660 | 1/1978 | Beck | 604/280 |
| 4,432,758 | 2/1984 | Finegold | 604/264 |
| 4,512,769 | 4/1985 | Kozam et al. | 604/264 |
| 4,588,395 | 5/1986 | Lemelson | 604/218 |

FOREIGN PATENT DOCUMENTS

| | | | |
|---|---|---|---|
| 0104878 | 12/1926 | Austria | 604/218 |
| 0609894 | 8/1926 | France | 604/59 |

Primary Examiner—Stephen C. Pellegrino
Attorney, Agent, or Firm—Lyon & Lyon

[57] ABSTRACT

The invention comprises an assortment of plunger-type syringes for the surgical implantation of granular ceramic substances such as hydroxyapatite, whitlockite and alpha alumina during alveolar ridge augmentation and repair. The barrels of the syringes, which are inserted into the patient's periosteal and gum tissue, have various lengths and radii of curvature and various degrees of tip bevelling, such that the surgeon can select the barrel configuration that most closely complies with the contours of the particular alveolar ridge portion upon which the augmentation surgery is to be performed in a particular case. The surgery can thus be performed with fewer and smaller incisions, less tissue trauma, lower risk of accidental tearing and puncturing of tissue, and lower risk of infection than possible with the apparatus and methods known to the prior art.

34 Claims, 2 Drawing Sheets

SYRINGE APPARATUS AND METHOD FOR THE SURGICAL IMPLANTATION OF GRANULAR SUBSTANCES

BACKGROUND OF THE INVENTION

The field of the present invention is apparatus and methods for the surgical implantation of granular substances. A number of injuries, diseases and other conditions are known to the medical and dental sciences which can cause atrophy of the bones forming the alveolar ridges of the human upper jaw (maxilla) and lower jaw (mandible). When alveolar ridge atrophy is sufficiently far advanced, the patient may even be unable to wear dentures because the ridges are insufficient to anchor them. In such cases, and in other situations where it is deemed medically desirable to arrest or repair alveolar ridge injury or deterioration, various surgical procedures can be employed to augment the alveolar ridges.

A traditional procedure for alveolar ridge augmentation is known as the "fifth rib" procedure, wherein each of the patient's fifth ribs is removed and bone therefrom engrafted upon the alveolar ridges. The "fifth rib" procedure involves major surgery, the disadvantages of which include not only substantial expense and patient discomfort but also a risk of infection and other complications that is multiplied by the fact that the procedure necessarily involves multiple surgical sites.

An alternative to the "fifth rib" procedure, employed with increasing frequency and success in recent years, involves the use, instead of bone from the patient's ribs, of granules of a biocompatible ceramic substance having a unique pore structure that supports and encourages the ingrowth of the patient's own maxillar and mandibular bones. Ceramics known to have suitable biocompatability properties include hydroxyapatite, whitlockite, and alpha alumina. See, e.g.: Jarcho, M.: "Calcium Phosphate Ceramics As Hard Tissue Prosthetics", *Clin. Orthoped.* 157: 259 (1981); Rothstein, S. et al., "Use of Hydroxyapatite for the Augmentation of Deficient Alveolar Ridges", *J. Oral Maxillofac. Surg.* 42: 2, 224–230 (1984); Kent, J. et al., "Reconstruction of the Atrophic Alveolar Ridge With Hydroxyapatite: A Five Year Report", Study presented at the Second World Congress of Bio-materials, Washington, D.C., Apr. 27–May 1, 1984; Cohen, D. W., ed., "Report of a Clinical Conference on a New Implant Material for Ridge Augmentation and Preprosthetic Preparation of the Edentulous Patient", *The Compendium of Continuing Education in Dentistry,* Suppl. No. 2, S45–S86 (1982).

By the use of certain hydrothermal chemical exchange processes, carbonate skeletal materials from certain specific marine organisms can be converted into hydroxyapatite or whitlockite replicas that retain a structure of completely interconnecting pores whose dimensions closely approximate those of human cancellous bone. The characteristics of these materials and methods of making them are disclosed in Roy, U.S. Pat. No. 3,929,971. Related technologies are disclosed in White, et al., U.S. Pat. No. 3,890,107.

Preparations of porous biocompatible ceramics, in granular form suitable for surgical implantation, are now commercially available to oral surgeons through several suppliers.

The use of ceramic granule implants has several advantages over the "fifth rib" procedure: it is not only less expensive and less painful, but because it involves fewer surgical sites, it lessens the risk of infection and other complications.

An early but still-used technique for applying growth-supporting ceramic substances to the maxilla and mandible involves incisions through the gum tissue along the whole length of the area to be augmented. The bone is then typically scraped until a fresh bleeding surface is exposed, the ceramic deposited in granular form and the gum tissue sutured over the deposit.

The most recent technique involves the use of syringes to implant the ceramic substances in granular form at sites along the alveolar ridges remote from the incision sites. The advantage of this technique over the earlier implantation technique is that it involves smaller incisions, and less suturing, resulting in less tissue trauma, less patient discomfort and lower risk of infection and other complications.

In the syringe implantation technique, the ceramic substance in granular form is usually mixed within the syringe with a saline solution or with blood taken from the patient. The syringe typically includes a hollow, cylindrical barrel with an opening at each end. A plunger is slidably inserted into an opening at the distal end of the barrel. There is typically a porous filter over the opening at the distal end of the barrel which prevents the granules from escaping but allows liquids to enter the barrel. After the ceramic granules and the liquid are mixed, the filter is removed so that the mixture can be extruded from the syringe.

A tunnel is then surgically formed under the periosteum of the maxilla or mandible to be augmented. The delivery of the ceramic granule/liquid mixture to the alveolar ridge repair site requires one or more incisions. Though the location of the incision depends upon the particular repair, an incision is typically made near the canine teeth in mandibular augmentation and at the mid-line of the gum, as viewed from above, in maxillar augmentation. Following tunnel formation, the distal end of the syringe barrel is inserted into the sub-periosteal tunnel and is guided to the location, remote from the incision, where the augmentation is to begin. As the syringe is withdrawn through the sub-periosteal tunnel, its contents are gradually extruded, leaving the sub-periostel tunnel packed with the ceramic granule mixture. After the syringe is fully withdrawn, the incision is sutured closed and the deposited ceramic granules may, if necessary, be manipulated into optimal position.

While guiding the syringe along the sub-periosteal tunnel, the surgeon must take great care to avoid puncturing the periosteum or the overlying gum tissue. Where the augmentation site is remote from the incision, it is difficult to avoid puncture if a conventional straight syringe barrel is used. The reason is that the alveolar ridge, viewed from above or below, is not straight but curved, describing an approximate semi-circle. Thus, when the ceramic granule mixture is to be deposited at a site on the posterior portion of the ridge, the syringe barrel, at the point of incision, must be flexed outward against the tissue so that the distal opening will follow as closely as possible the curve of the ridge. The flexing may tear the tissue at the incision, or necessitate a larger incision or additional incisions. If the syringe is not flexed outward at the incision, then the distal end of the syringe barrel, as it moves toward the posterior part of the ridge, will be pushed increasingly outward against the periosteum and the gum tissue and will likely result in tearing of those tissues. The mandibular ridge is curved in an even more complex fashion than the maxillar ridge. The mandibular ridge is not only roughly semicircular when viewed from above or below, but is seen to arch upward posteriorly as viewed from the side. Thus, the problems encountered in using the conventional straight syringe are even more acute in mandibular surgery than in maxillar surgery.

Presently on the market are several brands of ceramic granules intended for use in alveolar ridge augmentation and other periodontal repairs. Implantation syringes are typically sold together with the granules, which are packaged either in separate ampules or within pre-filled, sterilized syringes. Common elements of all now-available syringes are a simple, straight barrel configuration and a straight tip, that is, a tip truncated at a right angle to the longitudinal axis of the barrel. No supplier currently offers a granule implantation syringe that is in any wise adjustable in terms of barrel curvature or tip configuration, nor does any supplier currently offer an array of syringes which differ in barrel curvature or tip configuration. Nor does any presently-available granule implantation syringe contain any means for varying the orientation of the barrel with respect to the finger support component.

SUMMARY OF THE INVENTION

The present invention is directed to achieving a syringe apparatus, and a method for using it, which will enable an oral surgeon not only to minimize the size and number of incisions needed to accomplish an alveolar ridge augmentation procedure using ceramic granule implantation, but also to minimize the risk of punctures, tears, and other trauma to periosteal and gum tissue during the implantation procedure. In the embodiment herein described, the invention includes a reusable plunger and finger support assembly fitted at its distal end with a collet by means of which hollow, cylindrical syringe barrels may be rigidly but impermanently attached to the plunger and finger support assembly to make up the completed syringe. The barrel can be rotated in the collet before the collet is tightened, thus providing a means whereby the orientation of the barrel with respect to the finger support component can be varied as desired. The plunger cooperates with a piston attached to its distal end which closely fits within the bore of the hollow, cylindrical syringe barrel. The plunger stem is flexible, so that the piston can be made to pass through the bore of the barrel whether it be straight or curved. The invention, in its embodiment herein described, also includes an assortment of syringe barrels having various dimensions of length and curvature, such that the surgeon can choose the barrel that is most closely compatible with the contour of the particular alveolar ridge portion to be augmented in any particular case.

The invention, in the embodiment described herein, also includes syringe barrels having varying tip configurations, some tips being truncated at a right angle to the axis of the barrel at its distal end to form a straight tip, and others being truncated at an acute angle to form a bevelled tip. The assortment of straight and bevelled tips enables the surgeon to choose the tip configuration best suited to the particular augmentation being performed. Where the repair site is directly below the incision or very close thereto, a straight tip will usually provide the easiest and most accurate control of the positioning of the implanted granules. Where the site of the augmentation extends some distance from the incision site, so that a sub-periosteal tunnel of considerable length must be followed, a bevelled tip will usually provide at least four advantages over a straight tip: (1) the bevel will make it easier for the surgeon to insert the tip under the cut edge of the periosteum; (2) the bevel will reduce the force and effort required to push the syringe barrel along the route of the sub-periosteal tunnel; (3) a bevelled tip will tend to cause less tissue trauma than will a straight tip when pushed along the alveolar ridge in following the sub-periosteal tunnel; and (4) the bevelled tip will make it easier for the surgeon to guide the syringe accurately through the sub-periosteal tunnel from the point of incision to the remote end of the augmentation site.

The invention, in the embodiment described herein, also includes the use of syringe barrels that have been pre-filled with pre-measured quantities of sterile ceramic granules and plugged.

Taken together, the various elements of the invention provide a ready and convenient means whereby a surgeon can make up a syringe (or select a ready-made syringe) having that combination of barrel length, barrel curvature, tip configuration and granule volume which the surgeon judges to be optimal for the particular granule implantation procedure at hand.

DETAILED DESCRIPTION OF THE INVENTION

Figure 1:
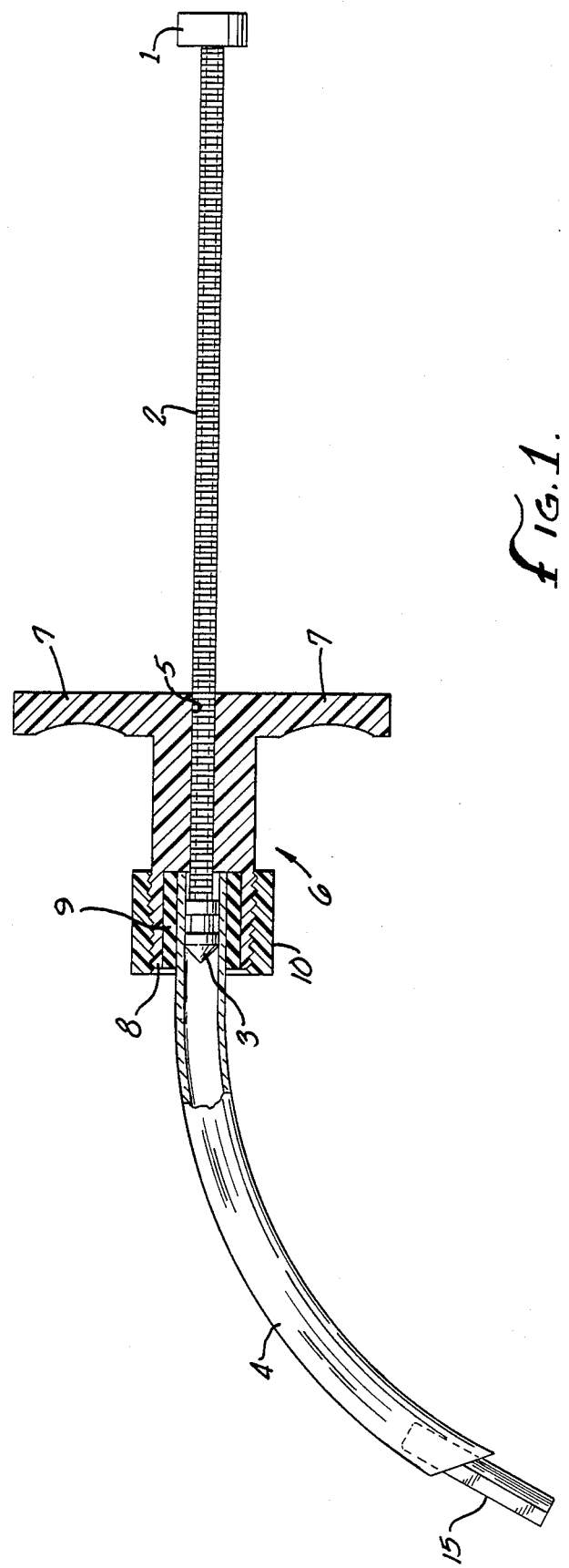
FIG. 1 is a partial cross section about the longitudinal axis of a syringe for the surgical implantation of granular substances, made up of a disposable, hollow cylindrical syringe barrel, having a straight portion at its proximal end, a curved distal portion and a bevelled tip. The barrel is rigidly but impermanently attached, by means of a collet, to a reusable assembly comprising a finger support, a plunger having a flexible stem and a longitudinal hole through which the stem of the plunger passes and is guided.

Turning now to the drawings, FIG. 1 illustrates an assembled syringe comprising a plunger button (1) rigidly attached to the proximal end of a flexible plunger stem (2). Attached to the distal end of the plunger stem (2) is a plunger piston (3) which is closely and slidably fitted within a hollow cylindrical syringe barrel (4). The plunger stem is slidably and rotatably mounted through a plunger guide-hole (5) which penetrates through the longitudinal axis of the finger support component (6). The finger support component (6) includes a plurality of finger support projections (7) generally perpendicular to its longitudinal axis and having any configuration such that they may conveniently be grasped by fingers of a human hand while the thumb of that hand is positioned to push upon the plunger button (1). The finger support component also includes, at its distal end, an annular collar (8) which extends longitudinally and opens in the distal direction. The annular collar (8) is concentric about the plunger guide-hole (5) and is penetrated at generally evenly-spaced points along its circumference by a plurality of longitudinal slots. The annular collar (8) bears on its outer surface male screw threads. The annular collar (8) has an inner surface suitably relieved and configured to accommodate an annular cylindrical gasket of an elastomeric material (9). Both the annular collar (8) and the cylindrical gasket (9) have inner diameters such that the proximal ends of interchangable hollow cylindrical syringe barrels (4) may be inserted by hand into the annular collar (8) when the gasket (9) is in position. The male threads on the outer surface of the annular collar (8) cooperate with the female threads on the inner surface of a locking ring (10) whose inner surface is tapered so that the inner diameter of the locking ring decreases from the proximal to the distal direction. The effect of the cooperation of the locking ring (10) and the annular collar (8) is such that if the threads of the locking ring (10) are engaged with the threads of the annular collar (8), and if the locking ring (10) is then rotated so as to cause it to move in the proximal direction, the action of the locking ring's taper upon the annular collar (8) exerts a clamping force which causes the collar and the gasket (9) positioned therein to tighten about the proximal end of a hollow cylindrical syringe barrel (4) which has been inserted into the collar and gasket and rotated therein to achieve the desired orientation of the finger support component with respect to the barrel. The result is that the hollow cylindrical syringe barrel (4) is rigidly but impermanently held within the collet assembly which comprises the annular collar (8), gasket (9), and locking ring (10).

The particular configuration and mode of operation of the collet as illustrated are meant to be neither critical nor limiting. Embodiments using other types of collets are equally within the scope and spirit of the invention, including without limitation threaded collets in which closure is accomplished by moving the locking ring in a distal rather than a proximal direction, and collets of both distally and proximally locking design which are not threaded and which depend on sliding friction and/or camming action to maintain closure.

Figure 2:
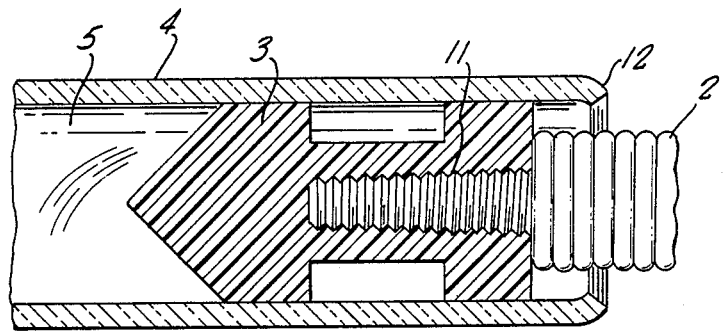
FIG. 2 is an enlarged partial cross section about the longitudinal axis of the plunger piston and stem, showing the cooperation between the male threaded plug at the distal end of the plunger stem with the female threaded hole on the proximal face of the plunger piston within the hollow cylindrical syringe barrel.

FIG. 2 illustrates a means of permanently coupling the plunger stem (2) to the plunger piston (3). After the barrel (4) has been locked into the collet, the plunger is pushed in the distal direction until the male threaded plug (11) at the distal end of the plunger stem is in contact with the female threaded opening on the proximal face of the plunger piston (3). The plunger is then pushed and rotated until the threads of the plug (11) are fully engaged with those of the piston (3). Once the threads are so engaged, the plunger piston becomes slidably movable in either direction by pushing or pulling on the plunger button.

In the illustrated embodiment of the invention, the plunger piston (3) is supplied as part of the interchangable and disposable pre-filled hollow cylindrical barrel (4) rather than as part of the reusable finger support component, plunger and collet assembly. The cylindrical barrel (4) has a constriction at the proximal end thereof to prevent the plunger piston from being fully withdrawn from between the walls of the barrel (4), so that a seal is always maintained to prevent any contaminants on or in the reusable portion of the syringe assembly from entering the proximal end of the barrel to contaminate the sterile granules contained therein. In the illustrated embodiment, the barrel (4) is of glass, and the constriction is formed by creating a slight crimp or reverse flare (12) according to well-known glass blowing techniques.

The particular means of coupling the plunger piston to the plunger stem as illustrated is meant to be neither critical nor limiting. Embodiments using other types of linkages are equally within the scope and spirit of the invention, including without limitation embodiments employing a piston which is reusable rather than disposable and which is permanently attached to the plunger stem.

Figure 3:
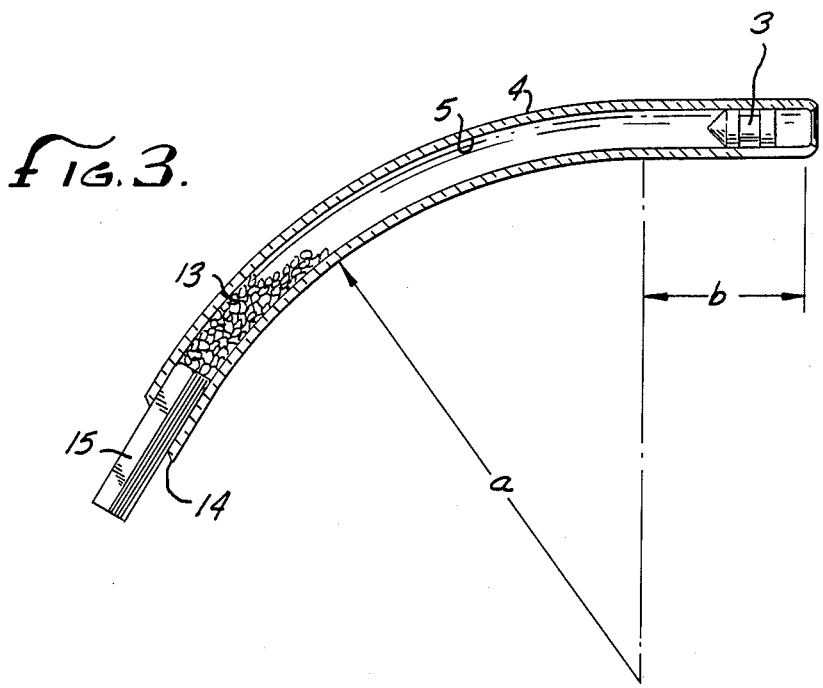
FIG. 3 is a partial cross section about the longitudinal axis of a disposable, hollow cylindrical syringe barrel, filled partially with a ceramic granular substance suitable for surgical implantation, said barrel having a straight proximal portion, a curved distal portion, a bevelled tip, a polyhedral plug inserted within the distal end thereof and a plunger piston inserted near the proximal end thereof.

FIG. 3 illustrates a hollow cylindrical barrel (4) in which has been inserted, near the proximal end, a plunger piston (3). The barrel has been partially filled with sterile ceramic granules (13) suitable for surgical implantation in alveolar ridge augmentation or repair. The bevelled tip (14) has inserted therein a polyhedral elastomeric plug (15) which acts as a filter. The plug, which is the subject of a co-pending U.S. patent application by James R. Swaniger and Reizo R. Sayano (Ser. No. 688,304, filed Jan. 2, 1985) is shown here merely for purposes of clarity.

The hollow cylindrical syringe barrel shown in FIG. 3 has a straight portion at its proximal end extending a length "b". In the preferred embodiment, a length of approximately 0.8 inches is used. However, this dimension is meant to be neither critical nor limiting, since all that is necessary to the proper functioning of the collet is that there be a sufficient straight bearing surface at the proximal end of the barrel to allow the barrel to be held in the collet in a straight, sturdy and rigid manner. In the embodiment shown in FIG. 3, the barrel (4) has a curved portion whose axis describes a portion of the circumference of a circle having a radius "a". This radius may vary over a considerable range, so as to comply closely with the radii of curvature of the mandibular and maxillar bones of a wide range of surgical subjects. A radius of 5 inches, although probably too large for any human application, will be useful for certain large animal veterinary applications, while for very small humans a radius as short as about 0.5 inches may be useful. A radius of 0.5 inches probably represents about the technical lower limit of the "a" dimension for at least two reasons. The first is that with radii shorter than about 0.5 inches, one is likely to encounter an unacceptably great tendency toward clogging of granules during extrusion. It is not feasible to remedy this problem by using smaller granules, since a granule must have at least one pore if it is to be fully efficatious in promoting bone ingrowth; and as granule size decreases, the likelihood increases that granules will lack pores. Thus, granule sizes of less than about 0.425 mm. are undesirable for clinical reasons. Secondly, as radii approach 0.5 inches or shorter, barrels become increasingly difficult to fabricate without flaws that will impede granule extrusion. The invention contemplates the availability of interchangable barrels having a sufficient variety not only in radii of curvature but also in lengths to achieve a high degree of compliance with alveolar ridges of all dimensional variations which may practically be encountered.

Figure 4A:
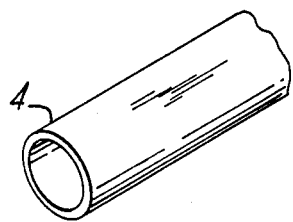
FIG. 4A is a perspective view of a straight syringe barrel tip.
Figure 4B:
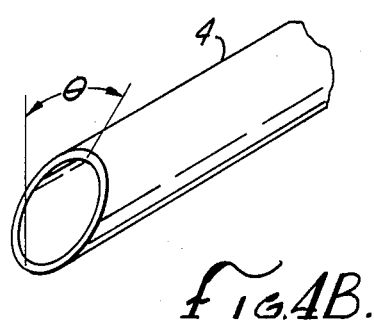
FIG. 4B is a perspective view of a bevelled syringe barrel tip.

FIGS. 4A and 4B illustrate differences in tip configurations at the distal ends of the hollow cylindrical syringe barrels. FIG. 4A shows a straight tip configuration, that is, a barrel truncated at an angle of 90° to its longitudinal axis. The barrel shown in FIG. 4B has a bevelled-tip configuration, that is, it is truncated at an angle of 45° to the axis of the barrel. The use of the 45° angular dimension in the illustration is meant be neither critical nor limiting, however, because particular applications in particular surgical situations may render it more appropriate to employ a tip bevelled to a greater or lesser angle.

Thus, what is disclosed is a set of plunger-type syringes which, because of assorted variations in the lengths, curvature radii and tip configurations of the hollow cylindrical barrels thereof, enable a surgeon using such syringes to minimize the size and number of incisions necessary in the surgical implantation of ceramic granules in alveolar ridge augmentation and repair, while at the same time minimizing the amount of tissue trauma involved in the procedure and minizing the risk of accidental penetration or tearing of gum and periosteal tissues. The syringe assortment may comprise a single reusable finger support, plunger and collet assembly and a set of interchangable barrels attachable thereto, or, as an alternative embodiment, it may include an assortment of fully self-contained and fully disposable syringes having a variety of lengths, curvature radii and straight and bevelled tip configurations.

Similarly, the assortment may comprise syringes or barrels which are supplied either pre-filled with ceramic granules or empty, to be filled by the surgeon with granules from a separate source.

As will be apparent to those skilled in the art in light of the preceding disclosure, many modifications, alterations, substitutions and uses are possible in the practice of this invention without departing from the spirit and scope thereof. The invention, therefore, is not to be restricted except in the spirit of the appended claims.

What is claimed is:

1. A kit of plunger type adjustable syringes for human and veterinary surgical implantation of granular substances to augment the maxillar and mandibular bones in the region of the alveolar ridges to permit alveolar ridge augmentation and repair while minimizing the size and number of necessary incisions, the amount of gum and periosteal tissue trauma and the risk of accidental penetration or tearing of gum and periosteal tissues, said kit comprising:
    (a) a single, finger support component comprising:
        finger support means;
        a plunger guide-hole which penetrates through a longitudinal axis of said finger support component;
        a plunger comprising a flexible plunger stem slidably and rotatably mounted in and through said plunger guide-hole, said stem having at the proximal end thereof a plunger button and at the distal end thereof a plunger piston, and
        an attachment means for rigidly but impermanently attaching hollow, cylindrical barrel to said finger support component, and
    (b) a set of interchangeable hollow cylindrical barrels each attachable to said finger support component, each of said barrels having bore dimensions such that said plunger piston will fit closely and slidably within the bore of the barrel, said barrels having proximal portions whose axes describe straight lines and each of said barrels being different from the others in one or more of their radii of curvature at their distal portions, lengths and tip configurations, thereby to achieve compliance with alveolar ridges of varying dimensions.

2. A kit as recited in claim 1 wherein the proximal portions of said barrels are between 0.4 and 1.2 inches in length.

3. A kit as recited in claim 1 wherein the distal portion of each said barrels has an axis which describes a portion of the circumference of a circle having a radius between one-half inch and five inches.

4. A kit as recited in claim 1 wherein the proximal portions of said barrels are between 0.4 and 1.2 inches in length and the distal portion of each of said barrels has an axis which describes a portion of the circumference of a circle having a radius between one-half inch and five inches.

5. A kit as recited in any one of claims 1-4, inclusive, wherein said tip configurations include at least one tip truncated at a right angle to the axis of the barrel at its distal end and at least one tip truncated at an acute angle to the axis of the barrel at its distal end.

6. A kit as recited in claim 5 wherein at least one tip truncated at an acute angle to the axis of the barrel at its distal end is truncated at an acute angle of 45 degrees.

7. A kit as recited in claim 1 wherein said attachment means for rigidly but impermanently attaching a hollow, cylindrical barrel to said finger support component comprises a collet.

8. A kit as recited in claim 7 wherein said collet is a threaded collet.

9. A kit as recited in claim 7 wherein said collet is an unthreaded collet.

10. A kit as recited in claim 9 wherein said unthreaded collet is a distally locking unthreaded collet.

11. A kit as recited in claim 9 wherein said unthreaded collet is a proximally locking unthreaded collet.

12. A kit as recited in claim 10 or claim 11 wherein said unthreaded collet depends upon sliding friction, camming action or both to maintain closure.

13. A kit as recited in claim 12 wherein said unthreaded collet comprises:
    an annular collar positioned at the distal end of said finger support component generally concentric about said plunger guide holes, penetrated by one or more longitudinal slots, opening in a distal direction and relieved at its distal opening to receive an annular cylindrical gasket of elastomeric material configured to receive the proximal end of each of said hollow cylindrical barrels, and
    a locking ring having an inner surface tapered to increase from a proximal toward a distal direction, slidably mounted upon said finger support component for movement between a proximal position at which said ring is disengaged from said annular collar and a distal position at which said ring is engaged with said annular collar, thereby to exert a clamping force on said annular collar.

14. A kit as recited in claim 1 wherein each of said barrels is filled with a pre-measured quantity of a sterile granular substance and plugged at the proximal end thereof by a plunger piston and at the distal end thereof by a polyhedral elastomeric ring.

15. A kit as recited in claim 14 wherein said sterile granular substance comprises biocompatible ceramic granules having a pore structure such as to promote bone and tissue ingrowth.

16. A kit as recited in claim 15 wherein said biocompatible ceramic granules comprise hydroxyapatite, whitlockite, alpha alumina or a mixture of two ro more of said substances.

17. A kit as recited in claim 15 wherein said biocompatible ceramic granules comprise hydroxyapatite.

18. A kit as recited in any one of claims 14–17, inclusive, wherein the proximal portions of said barrels are between 0.4 and 1.2 inches in length, the distal portion of each of said barrels has an axis which describes a portion of the circumference of a circle having a radius between one-half inch and five inches and said tip configurations include at least one tip truncated at a right angle to the axis of the barrel at its distal end and at least one tip truncated at an acute angle to the axis of the barrel at its distal end.

19. A kit of plunger type adjustable syringes for human and veterinary surgical implantation of granular substances to augment the maxillar and mandibular bones in the region of the alveolar ridges to permit alveolar ridge augmentation and repair while minimizing the size and number of necessary incisions, the amount of gum and periosteal tissue trauma and the risk of accidental penetration or tearing of gum and periosteal tissues, said kit comprising:
(a) a single, finger support component comprising:
a finger support means;
a plunger guide-hole which penetrates through the longitudinal axis of said finger support component;
a flexible plunger stem slidably and rotatably mounted in and through said plunger guide-hole, said stem having at the proximal end thereof a plunger button,
an attachment means for rigidly but impermanently attaching a hollow, cylindrical barrel to said finger support component, and
means for securely but impermanently coupling the distal end of said plunger stem to a plunger piston, and
(b) a set of interchangeable hollow cylindrical barrels each attachable to said finger support component, each of said barrels containing a plunger piston couplable to the distal end of said flexible plunger stem and having bore dimensions such that said plunger piston will fit closely and slidably within the bore of the barrel, each of said barrels having a proximal portion whose axis describes a straight line, a distal portion whose axis describes a curve and a tip at the distal end thereof, said tip being truncated at an angle to the distal end, each of said barrels being different from the others in one or more of their radii of curvature at their distal portions, lengths and tip configurations, thereby to achieve compliance with alveolar ridges of varying dimensions, and a constriction at the proximal end of each of said barrels such that the size of the bore of each said barrel at the point of said constriction is smaller in at least one dimension than the size of said plunger piston.

20. A kit as recited in claim 18 wherein each of said barrels is filled with a pre-measured quantity of a sterile granule substance and plugged at the ends thereof.

21. A kit as recited in claim 20 wherein said sterile granular substance comprise biocompatible ceramic granules having a pore structure such as to promote bone and tissue ingrowth.

22. A kit as recited in claim 21 wherein said biocompatible ceramic granules comprise hydroxyapatite, whitlockite, alpha alumina or a mixture of two or more of said substances.

23. A kit as recited in any one of claims 18–22, inclusive, wherein the proximal portions of said barrels are between 0.4 and 1.2 inches in length, the distal portion of each of said barrels has an axis which describes a portion of the circumference of a circle having a radius between one-half inch and five inches and said tip configurations include at least one tip truncated at a right angle to the axis of the barrel at its distal end and at least one tip truncated at an acute angle to the axis of the barrel at its distal end.

24. A kit of fully self-contained and fully disposable plunger type adjustable syringes for human and veterinary surgical implantation of granular substances to augment the maxillar and mandibular bones in the region of the alveolar ridges to permit alveolar ridge augmentation and repair while minimizing the size and number of necessary incisions, the amount of gum and periosteal tissue trauma and the risk of accidental penetration or tearing of gum and periosteal tissues, each of said syringes each comprising:
(a) a finger support component comprising:
a finger support means;
a plunger guide-hole which penetrates through the longitudinal axis of said finger support component, and
a plunger comprising a flexible plunger stem slidably and rotatably mounted in and through said plunger guide-hole, said stem having at the proximal end thereof a plunger button and at the distal end thereof a plunger piston, and
(b) a hollow cylindrical barrel rigidly and permanently attached to said finger support component, said barrel having bore dimensions such that said plunger piston will fit closely and slidably within the bore of the barrel, said barrel having a proximal portion whose axis describes a straight line, a distal portion whose axis describes a curve and a tip at the distal end thereof, said tip being truncated at an angle to the distal end, said syringe making up said kit being selected so that the barrel of each of said syringes is different from the others in one or more of its radius of curvature at its distal portion, its length and its tip configuration, thereby to achieve compliance with alveolar ridges of varying dimensions.

25. A kit as recited in claim 24 wherein the proximal portion of each of said barrels is between 0.4 and 1.2 inches in length.

26. A kit as recited in claim 24 wherein the distal portion of each of said barrels has an axis which describes a portion of the circumference of a circle having a radius between one-half inch and five inches.

27. A kit as recited in claim 24 wherein the proximal portion of each of said barrels is between 0.4 and 1.2 inches in length and the distal portion of each of said barrels has an axis which describes a portion of the circumference of a circle having a radius between one-half inch and five inches.

28. A kit as recited in any one of claims 24–27, inclusive, wherein said tip configurations include at least one tip truncated at a right angle to the axis of the barrel at its distal end and at least one tip truncated at an acute angle to the axis of the barrel at its distal end.

29. A kit as recited in claim 28 wherein at least one tip truncated at an acute angle to the axis of the barrel at its distal end is truncated at an acute angle of 45 degrees.

30. A kit as recited in claim 24 wherein the barrel of each syringe in said kit is filled with a pre-measured quantity of a sterile granular substance and plugged at the ends thereof.

31. A kit as recited in claim 30 wherein said sterile granular substance comprises biocompatible ceramic granules having a pore structure such as to promote bone and tissue ingrowth.

32. A kit as recited in claim 31 wherein said biocompatible ceramic granules comprise hydroxyapatite, whitlockite, alpha alumina or a mixture of two or more of said substances.

33. A kit as recited in claim 32 wherein said bicompatible ceramic granules comprise hydroxyapatite.

34. A kit as recited in any one of claims 30–33, inclusive, wherein the proximal portion of each of said barrels is between 0.4 and 1.2 inches in length, the distal portion of each of said barrels has an axis which describes a portion of the circumference of a circle having a radius between one-half inch and five inches and said tip configurations include at least one tip truncated at a right angle to the axis of the barrel at its distal end and at least one tip truncated at an acute angle to the axis of the barrel at its distal end.

* * * * *